United States Patent [19]

Nowacki et al.

[11] Patent Number: 4,470,412

[45] Date of Patent: Sep. 11, 1984

[54] INHALATION VALVE

[75] Inventors: Christopher Nowacki, Arlington Heights; Alfred G. Brisson, Schaumburg, both of Ill.

[73] Assignee: Trutek Research, Inc., Arlington Heights, Ill.

[21] Appl. No.: 359,679

[22] Filed: Mar. 19, 1982

[51] Int. Cl.³ .............................................. A61M 16/00
[52] U.S. Cl. ........................ 128/200.18; 128/200.23
[58] Field of Search ...................... 128/200.18, 200.23, 128/205.24, 207.12, 206.15; 137/512.15, 512.4

[56] References Cited
U.S. PATENT DOCUMENTS

| | | | |
|---|---|---|---|
| 4,259,951 | 4/1981 | Chernack et al. | 128/200.18 X |
| 4,263,907 | 4/1981 | Lindsey | 128/200.18 |
| 4,333,450 | 6/1982 | Lester | 128/200.18 X |

FOREIGN PATENT DOCUMENTS 9667 4/1980 European Pat. Off. ....... 128/200.23

*Primary Examiner*—Edward M. Coven
*Attorney, Agent, or Firm*—Trexler, Bushnell & Wolters, Ltd.

[57] ABSTRACT

An inhalation valve is presented for use with a known antiasthmatic medication cartridge and mouthpiece to simplify patient inhalation and to improve mist formation. A cylindrical passageway receives the known mouthpiece and is provided with an elastomeric diaphragm having a slit therein. An upstream spider backs up the diaphragm. Upon inhalation the diaphragm flexes and stretches to open the slit, and the diaphragm seals off exhaust passages. On exhalation the diaphragm backs against the spider which seals the slit, the diaphragm moving away from and opening the exhaust passages.

9 Claims, 5 Drawing Figures

INHALATION VALVE

BACKGROUND OF THE INVENTION

A person suffering from asthma may when suffering an asthmatic attack have rather considerable trouble in breathing, due to swelling in the bronchi and due to secretion of mucus. There are various antiasthmatic pills that are effective, but which generally are somewhat slow-acting. There are also medications available for intravenous treatment which work quite rapidly, but which require administration by skilled medical personnel. For most patients the promptest, immediately available relief is by way of an inhalant. Epinephrine or other suitable asthmatic medication is packaged with a suitable diluent in a small pressurized cannister or cartridge which interfits with a mouthpiece. The patient places the mouthpiece in his mouth, and depresses the cartridge, thereby releasing a measured amount of medication which is inhaled through the mouthpiece.

Some patients do not inhale properly, and the mouthpiece may not be completely effective in cooperation with the cartridge to convert the medication into a mist which is deposited in the proper bronchial area to relieve the asthmatic attack. Often there are small droplets, rather than a mist, and this may be compounded by improper inhalation which results in much of the medication simply going into the throat and stomach where it is ineffective against the asthmatic attack.

OBJECTS AND SUMMARY OF THE INVENTION

In accordance with the present invention a valve accompanying an extended mouthpiece for a broncho dilator of the type just described is provided which aids the asthmatic sufferer in properly inhaling, and in breaking up droplets into a mist form.

Thus, the principle object of the present invention is to provide an improved valve for converting epinephrine or other broncho dilator into a proper mist for inhalation by a person suffering an asthmatic attack.

It is a further object to the present invention to provide a valve as just noted which is cooperable with a large number of existing commercial broncho dilator mouthpieces for providing improved mist and inhaling by the patient.

It further is an object of the present invention to provide a universal extension fitting for broncho dilators including a one-way valve which opens upon inhalation without bypassing any ambient air into the inhaled mist, and which closes upon exhalation with the exhaled breath bypassed and not entering into the chamber containing the broncho dilator mist.

In carrying out the foregoing and other objects and advantages, we have provided an extension fitting for broncho dilators having an elastomeric receiver fitting about the existing mouthpiece of a commercial broncho dilator device. This receiver is at the entering end of a cylinder, which cylinder has a mouthpiece at the opposite end. An elastomeric valve is provided between the cylinder and the mouthpiece, which valve comprises a generally flat diaphragm having a slit therein. Upon inhalation the diaphragm flexes to permit opening of the slit so that mist will pass through the cylinder into the bronchial passages of the asthmatic sufferer. When the patient exhales the diaphragm is forced flat against a supporting spider with the slit effectively sealed. Bypass openings are provided to permit exhaust of the exhaled breath into the atmosphere. These exhaust openings are closed by the diaphragm upon inhalation so that only the epinephrine or the like mist is inhaled without being mixed with ambient air.

THE DRAWINGS

The invention will best be understood with reference to the following test when taken in connection with the accompanying drawings, wherein.

DETAILED DISCLOSURE OF THE ILLUSTRATIVE EMBODIMENT

Figure 1:
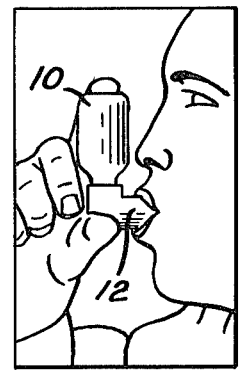
FIG. 1 is a view illustrating a broncho dilator device as found in the prior art.

Reference first should be made to FIG. 1 for an understanding of the prior art. A small pressurized cannister or cartridge, sometimes referred to as a nebulizer, is charged with epinephrine or other suitable antiasthmatic medication in a suitable diluent, and under pressure. The cartridge fits into a receiving end of right angle mouthpiece 12, the opposite end of which is placed in the asthmatic sufferer's mouth. The cartridge is pressed down, being squeezed between the index finger and the thumb underlying the mouthpiece. This causes a valve stem in the cartridge to press against a reaction base in the mouthpiece to discharge a measured quantity of medication into the mouthpiece. The discharge is supposed to be in a form of a mist, but in fact often contains small droplets. The patient inhales, and the mist passes into the mouth, and hopefully into the bronchial tubes to provide asthmatic relief. The patient is then supposed to hold his breath for a short time, and subsequently to inhale slowly through nearly closed lips. However, as noted heretofore, some of the medication may simply be in the form of droplets rather than mist, and the droplets generally do not reach the bronchial tubes to effect their intended purpose.

Figure 2:
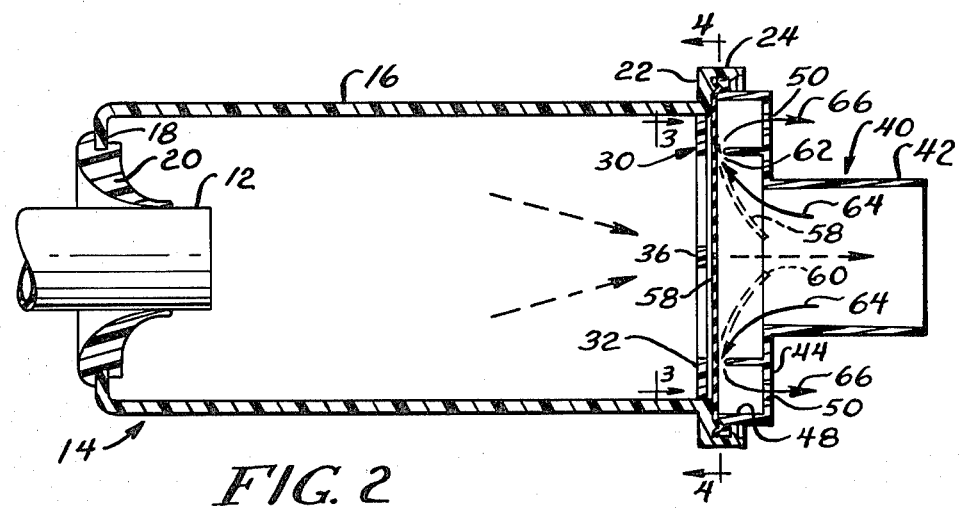
FIG. 2 is a side view partly in longitudinal section illustrating the novel inhalation valve forming the subject matter of the present invention.
Figure 3:
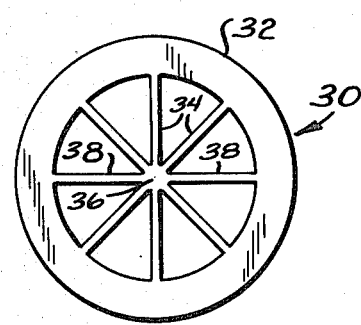
FIG. 3 is a cross-sectional view taken substantially along the line 3—3 in FIG. 2 illustrating the spider which backs up the elastomeric valve diaphragm.
Figure 2A:
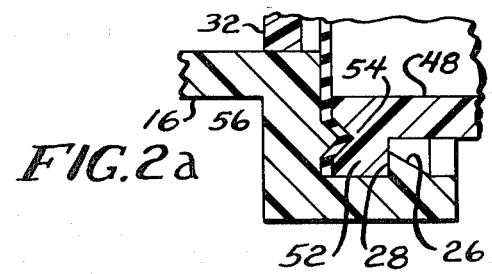
FIG. 2A is an enlarged detail view of a portion of FIG. 2 showing clamping of the diaphragm.
Figure 4:
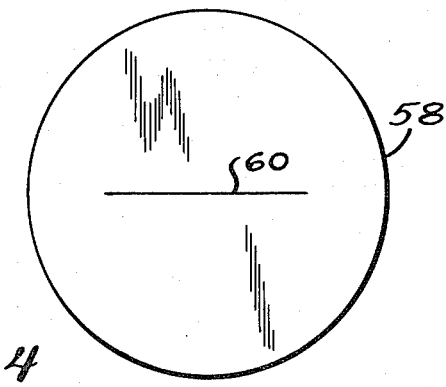
FIG. 4 is a cross-sectional view taken substantially along the line 4—4 showing the elastomeric diaphragm.

We have found that the drops can be broken up into a mist, and the patient can be more or less forced to inhale properly when the use of the inhalation valve forming the subject matter of the present invention, and for which reference should be had particularly to FIG. 2, and also to FIGS. 3 and 4.

As shown in FIG. 2 there is an inhalation valve 14 comprising a cylinder 16 preferably molded of a suitable plastic material. The cylinder is provided at its entering end (the left end in FIG. 2) with a radially inwardly directed flange 18 of limited extent. This flange retains a generally frustoconical elastomeric adaptor 20 which receives the mouthpiece 12 previously referred to. The frustoconical shape and the elastomeric nature of the adaptor 20 is such that mouthpieces of widely differing sizes and configurations can be securely gripped.

At the opposite end of the cylinder 16 there is an outwardly extending peripheral flange 22 having at its extremity an axially extending cylindrical flange 24. At its extremity the cylindrical flange 24 is provided with an internal taper 26 having a right angle shoulder or stop surface 28 behind it; 24, 26 can be spaced teeth.

Also at the exit end of the cylinder there is provided a spider 30 which is shown also in FIG. 3. The spider 30 may be molded integrally with the cylinder 16, but more conveniently is a separate plastic piece which is secured within the cylinder by known techniques, such as a cement, sonic welding, etc. The spider comprises an annular ring 32 having formed integrally therewith a plurality of radial ribs 34 joined together at the center at 36. As shown in FIG. 3 there are eight such ribs. The precise number is not critical, but there should be one pair of ribs extending diametrically across the spider, such pair in the present instance being identified by numeral 38. The fitting 14 further includes a mouthpiece element 40 having a generally cylindrical, slightly tapered mouthpipe 42 to be received in the person's mouth. The mouthpipe has at its entering end a radially extending flange or disc 44 which partway out is provided with a cylindrical flange 46 extending in the entering direction, opposite to the mouthpipe 42. At its periphery the disc 44 is provided with a cylindrical flange 48 also extending in the direction of the receiving end of the cylinder 16, i.e., opposite to the mouthpipe 42. Intermediate the cylindrical flanges 46 and 48 the disc 44 is provided with an annular array of spaced apertures 50 for exhaust of exhaled air.

The flange 48 is axially somewhat longer than the flange 46, as will be explained shortly, and it is provided at its extremity with a radially extending annular flange 52 which snaps over the tapered surface 26 and behind the shoulder 28 so that the mouthpiece element 40 is held in assembled position with the cylinder 16. The entering end face of the flange 52 is provided with an annular recess 54, and the confronting face of the flange 22 on the cylinder 16 is provided with a complementary rib 56.

An elastomeric diaphragm 58 is trapped between the flange 52 and the flange 22, being securely held in place by the complementary rib 56 and recess 54. As is particularly seen in FIG. 4, the diaphragm 58 is provided with a diametral slit 60 which in related position lies across the aligned ribs 38. As now will be seen, the relative shortness of the ring or flange 46 as compared with the flange 48 provides for clearance space 62 between the flange 46 and the diaphragm 58.

In order to use the present inhalation valve, the mouthpiece 12 of the prior art is inserted in the member 20, as previously described. The mouthpiece 22 is received in the mouth of the person suffering an asthmatic attack. The cartridge is pressed down in the mouthpiece to release a measured amount of medication, in accordance with the prior art. However, rather than the misted medication passing directly through the mouthpiece into the mouth of the person using it, the mist is passed into the cylinder 16. The elongated flow path provided by the cylinder allows further opportunity for droplets to atomize or evaporate into a mist. As the person inhales, the diaphragm 58 deflects toward the person's mouth, as illustrated in broken lines in FIG. 2, thus allowing the slit 60 to open, and thus to pass the misted medication. Movement of the medication past the spider 30, and past the edges of the slit, enhances evaporation or dispersion of droplets into the desired mist form. It is not necessary for the patient to engage in any artificial or learned process of breathing, since he need only inhale, and exhale. Upon exhalation the diaphragm returns to its initial flat position with the slit 60 sealing across the aligned ribs 38. Air passes through the clearance space 62 as indicated by the arrows 64, and out through the holes 50 as as indicated by the arrows 66. Upon inhalation the deflection of the diaphragm causes the diaphragm to press against the free end of the cylindrical flange 46, and thereby to prevent any outside air from being drawn in along with the medication. Floating of the diaphragm back and forth upon alternate inhalation and exhalation also aids in breaking up any droplets into mist form.

As noted, the parts are molded of suitable plastic material, with the exception of the diaphragm, which is an elastomeric material; silicone rubber is one particular material that has been found satisfactory for this purpose. The device is readily washed or cleansed in alcohol, and hence is capable of extended use. However, the cost of production is low, and it is not necessary to preserve the device indefinitely.

It will now be apparent that we have invented an improved valve or extension piece for use with a conventional broncho dilator inhalation device which would cooperate with a large number of prior art devices, which is remarkably easy for the asthmatic sufferer to use, and which provides improved formation of mist. The simplicity of inhalation for the asthmatic sufferer, and the improved misting result in more of the antiasthmatic medication ending up in the bronchi for relief of the asthmatic attack, thereby minimizing bypassing of the medication through the throat and stomach where it does no good.

The specific example of the invention as herein shown and described is for illustrative purposes only. Various changes will no doubt occur to those skilled in the art, and will be understood as forming a part of the present invention insofar as they fall within the spirit and scope of the appended claims.

The invention is claimed as follows:

1. An inhalation valve including an elongated body defining a passageway having an entering upstream end and an exit downstream end, means at said entering end for receiving structure for applying inhalation medication, a mouthpiece at said exit end for receipt in a patient's mouth, an elastomeric diaphragm having a central opening therein and an imperforate portion outwardly of the central opening, means engaging said diaphragm adjacent the periphery thereof and mounting said diaphragm adjacent said exit end transversely of said passageway, said diaphragm flexing downstream and freeing said opening for passage of medication upon inhalation by a patient, backup means immediately upstream of said diaphragm preventing flexing of said diaphragm upstream upon exhalation by a patient and including a member lying across said opening and against which said diaphragm is pressed upon exhalation to seal said opening to prevent retrograde flow upon exhalation, an annular flange extending upstream from said mouthpiece and terminating at a rim presenting a valve seat normally spaced from said diaphragm downstream thereof, exhaled air from said mouthpiece passing between said rim and said diaphragm, and exhaust port means disposed outwardly of said annular flange to exhaust exhaled air to the atmosphere, the imperforate portion of the diaphragm presenting a valve surface movable in unison with the portion of the diaphragm containing the central opening and juxtaposed to the rim valve seat in position for engagement thereagainst with flexing of said diaphragm upon inhalation and bringing the valve surface of said diaphragm into engagement with said rim valve seat to seal off said exhaust port means and disengagement from the rim valve seat upon exhalation to exhaust through the exhaust port means.

2. An inhalation valve as set forth in claim 1 wherein said central opening comprises a diametral slit.

3. An inhalation valve as set forth in claim 2 wherein said mouthpiece includes an annular transverse plate, a tubular portion extending downstream from said annular transverse plate adjacent the inner margin thereof for receipt in a patient's mouth, said annular flange being spaced outwardly of said tubular portion and extending upstream from said annular transverse plate.

4. An inhalation valve as set forth in claim 3 wherein said exhaust port means comprise openings in said annular transverse plate outwardly of said annular flange.

5. An inhalation valve as set froth in claim 2 wherein said backup means comprises a spider.

6. An inhalation valve as set forth in claim 1 wherein said mouthpiece includes an annular transverse plate, a tubular portion extending downstream from said annular transverse plate adjacent the inner margin thereof for receipt in a patient's mouth, said annular flange being spaced outwardly of said tubular portion and extending upstream from said annular transverse plate.

7. An inhalation valve as set forth in claim 6 wherein said exhaust port means comprise openings in said annular transverse plate outwardly of said annular flange.

8. An inhalation valve as set forth in claim 1 wherein said backup means comprises a spider.

9. An inhalation valve as set forth in claim 1 wherein said receiving means at said entering end comprises an open ended frusto-conical elastomeric member secured to the entering end of and extending into said body.

* * * * *